US007228741B2

(12) United States Patent
Georgeson et al.

(10) Patent No.: US 7,228,741 B2
(45) Date of Patent: Jun. 12, 2007

(54) ALIGNMENT COMPENSATOR FOR MAGNETICALLY ATTRACTED INSPECTING APPARATUS AND METHOD

(75) Inventors: Gary E. Georgeson, Federal Way, WA (US); Michael D. Fogarty, Auburn, WA (US)

(73) Assignee: The Boeing Company, Chicago, IL (US)

( * ) Notice: Subject to any disclaimer, the term of this patent is extended or adjusted under 35 U.S.C. 154(b) by 314 days.

(21) Appl. No.: 10/943,170

(22) Filed: Sep. 16, 2004

(65) Prior Publication Data

US 2006/0055396 A1 Mar. 16, 2006

(51) Int. Cl.
*G01N 9/24* (2006.01)

(52) U.S. Cl. .............................. 73/634; 73/639; 73/643; 73/644

(58) Field of Classification Search ................. 73/634, 73/639, 643, 644, 640, 641, 635
See application file for complete search history.

(56) References Cited

U.S. PATENT DOCUMENTS

| 4,167,880 | A |   | 9/1979 | George |          |
|-----------|---|---|--------|--------|----------|
| 4,311,052 | A |   | 1/1982 | Jeffras et al. | |
| 5,056,477 | A | * | 10/1991 | Linder et al. | ............ 123/90.17 |
| 5,297,408 | A | * | 3/1994 | Yoshida | ....................... 72/12.7 |
| 5,593,633 | A |   | 1/1997 | Dull et al. | |
| 5,902,935 | A |   | 5/1999 | Georgeson et al. | |
| 6,484,583 | B1 |  | 11/2002 | Chennell et al. | |
| 6,658,939 | B2 |  | 12/2003 | Georgeson et al. | |
| 6,722,202 | B1 |  | 4/2004 | Kennedy et al. | |
| 6,748,791 | B1 |  | 6/2004 | Georgeson et al. | |
| 2003/0154801 | A1 |  | 8/2003 | Georgeson | |
| 2003/0210027 | A1 |  | 11/2003 | Pedigo et al. | |
| 2003/0221306 | A1 |  | 12/2003 | Day et al. | |
| 2004/0103721 | A1 |  | 6/2004 | Georgeson | |
| 2006/0162456 | A1 | * | 7/2006 | Kennedy et al. | .............. 73/620 |

FOREIGN PATENT DOCUMENTS

EP     1 132 164 A2   9/2001
JP         9229911 A   9/1997

OTHER PUBLICATIONS

*Automated Ultrasonic Scanning System (AUSS®), Mobile Automated Scanner (MAUS®)* http://www.engineeringatboeing.com/mfgquality/quality/automatedsystems.html, Jun. 21, 2004, 4 pages.

(Continued)

*Primary Examiner*—Hezron Williams
*Assistant Examiner*—Jacques M. Saint-Surin
(74) *Attorney, Agent, or Firm*—Alston & Bird LLP

(57) ABSTRACT

An apparatus and method aligning magnetically coupled inspection probes are provided. In this regard, a tracking probe may be magnetically coupled to a driven probe and move in coordination therewith. An alignment compensator for magnetically coupled inspection probes offsets misalignments between a driven probe and a tracking probe. Misalignments between magnetically coupled probes may be caused by gravity, friction, and movement of the probes. An alignment compensator may use one or more magnets, or electromagnets, to improve the alignment of the probes. An alignment compensator may include a control system for adjusting the power to an electromagnet or repositioning a magnet to offset misalignment of probes.

41 Claims, 13 Drawing Sheets

OTHER PUBLICATIONS

*Non Destructive Testing*, http://www.aascworld.com/ndt-ttu.htm, Aug. 19, 2004, 3 pages.

*Inspection of In-Service Composite-Honeycomb Structures*, Aerospace Application Note: Rev.: Jan. 2002, R/D Tech.

*Probe Catalog 2003-2004*, Thru-Transmission Ultrasonics, NDT Engineering Corporation, R/D Tech Company, pp. 1-11.

*Air-Coupled Ultrasonic Inspection*, http://www.qmi-inc.com/AIRSCAN.htm, Aug. 19, 2004, 3 pages.

*AIRSCAN® Transducer Specifications*, http://www.qmi-inc.com/Airscan%20TX%20specifications.htm, Aug. 19, 2004, 18 pages.

U.S. Appl. No. 10/752,890, filed Jan. 7, 2004, In re: Bossi et al., entitled *Non-Destructive inspection Device for Inspecting Limited-Access Features of a Structure*.

U.S. Appl. No. 10/734,452, filed Dec. 12, 2003, In re: Bossi et al., entitled *Ultrasonic Inspection Device for Inspecting Components at Preset Angles*.

\* cited by examiner

ALIGNMENT COMPENSATOR FOR MAGNETICALLY ATTRACTED INSPECTING APPARATUS AND METHOD

CROSS-REFERENCE TO RELATED APPLICATIONS

The contents of co-pending applications filed concurrently herewith and entitled "Magnetically Attracted Inspecting Apparatus and Method Using a Fluid Bearing," "Magnetically Attracted Inspecting Apparatus and Method using a Ball Bearing," "Apparatus and Method for Area Limited-Access Through Transmission Ultrasonic Inspection," and "End Effector Inspection Apparatus and Method" are incorporated by reference in their entireties. The contents of U.S. Pat. No. 6,722,202 to Kennedy are incorporated by reference in its entirety.

FIELD OF THE INVENTION

The present invention relates generally to an apparatus and method for inspecting a structure and, more particularly, to an apparatus and method for aligning magnetically attracted probes for inspecting a structure.

BACKGROUND

Non-destructive inspection (NDI) of structures involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or flaws in the structure. Inspection may be performed during manufacturing of a structure and/or once a structure is in-service. For example, inspection may be required to validate the integrity and fitness of a structure for continued use in manufacturing and future ongoing use in-service. However, access to interior surfaces is often more difficult or impossible without disassembly, such as removing a part for inspection from an aircraft.

Among the structures that are routinely non-destructively tested are composite structures, such as composite sandwich structures and other adhesive bonded panels and assemblies. In this regard, composite structures are commonly used throughout the aircraft industry because of the engineering qualities, design flexibility and low weight of composite structures, such as the stiffness-to-weight ratio of a composite sandwich structure. As such, it is frequently desirable to inspect composite structures to identify any flaws, such as cracks, voids or porosity, which could adversely affect the performance of the composite structure. For example, typical flaws in composite sandwich structures, generally made of one or more layers of lightweight honeycomb or foam core material with composite or metal skins bonded to each side of the core, include disbonds which occur at the interfaces between the core and the skin or between the core and a septum intermediate skin.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo or mechanical impedance sensors may be used to provide indications of voids or porosity, such as in adhesive bondlines of the structure. High resolution inspection of aircraft structure are commonly performed using semi-automated ultrasonic testing (UT) to provide a plan view image of the part or structure under inspection. While solid laminates may be inspected using one-sided pulse echo ultrasonic (PEU) testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as TTU transducers, is typically processed by a processing element, and the processed data may be presented to a user via a display.

The non-destructive inspection may be performed manually by technicians who typically move an appropriate sensor over the structure. Manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning of structures is time-consuming, labor-intensive, and prone to human error.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For example, the Automated Ultrasonic Scanning System (AUSS®) system is a complex mechanical scanning system that employs through-transmission ultrasonic inspection. The AUSS system can also perform pulse echo inspections, and simultaneous dual frequency inspections. The AUSS system has robotically controlled probe arms that must be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides or surfaces of a structure which, at least in some circumstances, will be problematic, if not impossible, particularly for very large or small structures. To maintain the ultrasonic transmitter and receiver in proper alignment and spacing with one another and with the structure undergoing inspection, the AUSS-X system has a complex positioning system that provides motion control in ten axes. This requirement that the orientation and spacing of the ultrasonic transmitter and receiver be invariant with respect to one another and with respect to the structure undergoing inspection is especially difficult in conjunction with the inspection of curved structures.

Furthermore, manual, semi-automated, and automated scanning systems typically are limited in the size of a structure that can be inspected, generally limited to areas just a few meters square and typically limited to much smaller areas, although some larger, more complicated systems are available. Stiffness and weight limitations often restrict the distance a manual, semi-automated, or automated system may be able to extend inspection devices over a structure for inspection. Thus, large composite structures may not be capable of complete inspection. For example, contemporary inspection methods are not well suited for inspecting a Sea Launch payload fairing with a diameter of approximately four meters, a cylindrical length of approximately five meters, and an overall length of over twelve meters.

Additionally, alignment of various scanning systems is typically more complicated and requires more precision than can be provide by computer controlled robotic arms that are commonly used to align sensors. Alignment is especially important when using more than one scanning probe, such as for through transmission ultrasonic inspection. For example, gravity, friction, and movement often cause misalignment of one or more probes, or two probes with respect to each other when used as a pair.

Accessibility to the structure requiring inspection and particular features thereof is one consideration in choosing a non-destructive inspection device. Access to the structure requiring inspection may be so limited that a manual inspection by a technician or a semi-automated or automated system is not possible, typically due to systems requiring access to exterior and interior surfaces of the structure to be inspected. For example, the backside of an inlet duct for an Unmanned Combat Air Vehicle (UCAV) or an F-35 has limited access for inspection. Alignment and positioning of sensors such as transducers is similarly complicated by accessibility to the structure such as inaccessibility to one side of a composite structure. Additionally, the ability to properly align the device or devices used for inspection and the accessibility to do so may also be considerations in choosing an inspection device or system and knowing the quality and limitations thereof.

Accordingly, a need exists for an improved non-destructive inspection device and method to inspect a structure.

SUMMARY OF THE INVENTION

An improved apparatus and method for inspecting a structure, such as a composite structure, especially a curved composite structure, compensates for misalignment of magnetically attracted probes. An inspection apparatus or method using an alignment compensator of the present invention may advantageously improve inspection of a structure, such as continuous inspection of a large area of a structure, by maintaining alignment and positioning of sensing transducers and/or receivers. The method and apparatus of the present invention use probes including respective sensing elements, such as ultrasonic transducers, that are disposed proximate the opposed surfaces of a structure. Only one of the probes need be driven. Either probe or both probes may include an alignment compensator for aligning the two probes with respect to each other. However, because only one probe need be driven, the probes may not be accurately aligned beyond the rough alignment provided by the magnetic coupling between the probes. Thus, the method and apparatus of the present invention are advantageously adapted to align probes for inspection of structures in which a surface of the structure is relatively inaccessible. Further, embodiments of the method and apparatus of the present invention permit alignment of probes that may be suspended against and glide or contact and ride along the respective surfaces of the structure. Thus, embodiments of the present invention may reduce the necessary sophistication of the motion control system that is otherwise required by conventional scanning systems to maintain the ultrasonic probes in a predefined orientation and at a predefined spacing from the respective surface of a structure undergoing inspection and may maintain alignment between the probes or the sensors of the probes.

An apparatus of the present invention may include a single alignment compensator on one probe, multiple alignment compensators on one probe, or one or more alignment compensators on magnetically attracted probes. Generally, an alignment compensator is a device or system used to compensate for external forces acting on an apparatus that act to misalign a probe of the apparatus such that by using the alignment compensator, the probes of the apparatus are maintained in alignment. An alignment compensator may be a permanent magnet or an electromagnet. An alignment sensor, such as a linear encoder, may be used with a controller and a power supply to control the magnet to align a probe with another probe.

According to another aspect of the present invention, a method of aligning probes for inspecting a structure is provided. In this regard, the driven probe is positioned proximate the first surface of the structure, and the tracking probe is positioned proximate the opposed second surface of the structure. At least one of the probes includes an alignment compensator. The method of aligning the probes includes measuring the misalignment of the sensors of the probes and compensating for the misalignment. Compensating for the misalignment may be performed using a single magnet, such as a permanent magnet. Alternatively, compensating for the misalignment may be performed using more than one magnet. Compensating for misalignment may include adjusting the power to an electromagnet to modify the strength of the magnetic field produced by the electromagnet. A controller may be used to adjust the power to the electromagnet. The method of aligning the probes may include measuring the strength of a signal transmitted from one probe to the other or calculating the signal-to-noise ratio and adjusting the power to an electromagnet to increase the signal or the signal-to-noise ratio. One or more alignment compensators of the present invention may be used for aligning probes in different positions and for movement in any direction. As positions change and as movement changes, one or more alignment compensators or an alignment compensator system may adjust or compensate for the change to maintain alignment of the probes.

These and other characteristics, as well as additional details, of the present invention are further described in the Detailed Description with reference to these and other embodiments.

BRIEF DESCRIPTION OF THE DRAWING(S)

Having thus described the invention in general terms, reference will now be made to the accompanying drawings, which are not necessarily drawn to scale, and wherein:

Figure 16A:
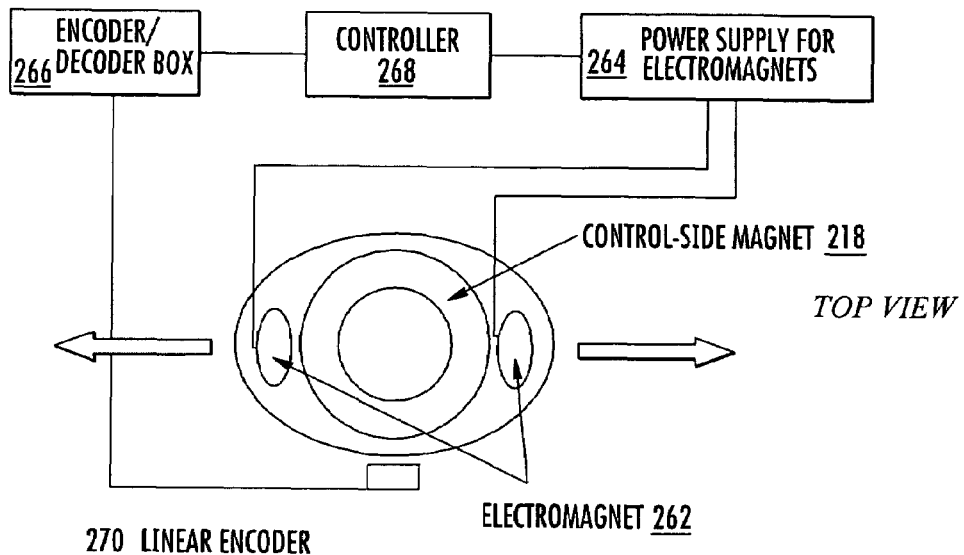
Figure 16B:
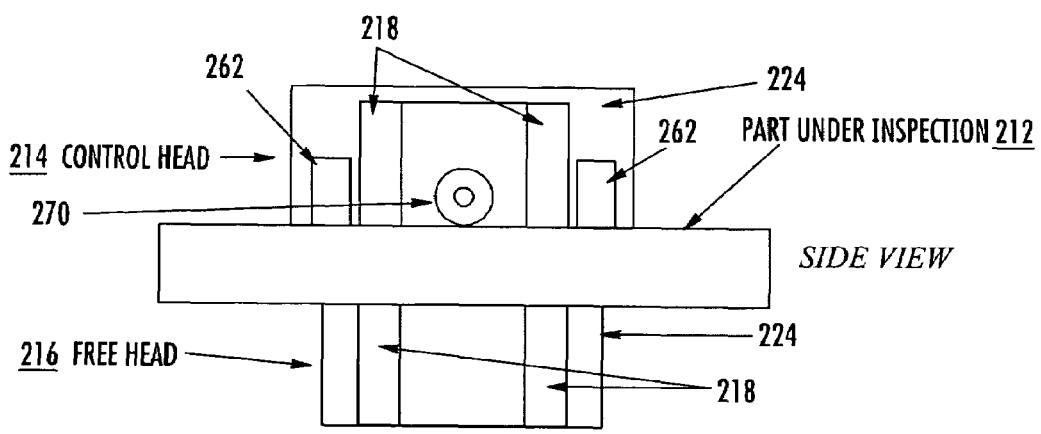

FIG. 16A is a schematic diagram of an embodiment of a probe with a ring magnet and an alignment compensator with two electromagnets and an alignment compensator of the present invention; and FIG. 16B is a schematic diagram of an embodiment of an apparatus with two probes, each with a ring magnet, where one probe has an alignment compensator with two electromagnets and an alignment sensor of the present invention positioned across the structure being inspected.

DETAILED DESCRIPTION

The present invention will be described more fully with reference to the accompanying drawings. Some, but not all, embodiments of the invention are shown. The invention may be embodied in many different forms and should not be construed as limited to the embodiments described. Like numbers and variables refer to like elements and parameters throughout the drawings.

Alignment compensators are described with respect to an apparatus having magnetically attracted probes. The description of alignment compensators of the present invention appears under the heading Alignment Compensation in Section II and follows this description of magnetically attracted probes.

I. Magnetically Attracted Inspection Probes

An apparatus having magnetically attracted probes includes a driven probe disposed proximate a first surface of the structure and a tracking probe disposed proximate an opposed second surface of the structure. The driven probe is moved along the first surface of the structure. The tracking probe follows along the second surface of the structure in response to the movement of the driven probe under the magnetic attraction.

To facilitate the coordinated movement of the tracking probe in conjunction with the driven probe, both probes include magnets disposed to create an attractive force between them using typical magnetic forces of attraction. Ring magnets may be used in the probes.

A driven probe typically includes a sensing element for inspecting the structure as the driven probe moves along the first surface of the structure. While the sensing element may be an x-ray detector, a camera or the like, the sensing element is typically an ultrasonic transducer. Typically, the tracking probe also includes a sensing element, such as an ultrasonic transducer. The ultrasonic transducers of the driven and tracking probes may be an ultrasonic transmitter, an ultrasonic receiver, or both. A sensor of a probe, such as an ultrasonic transducer, may be positioned within a ring magnet of a probe; thus, as the ring magnets of the probes align the two probes on respective surfaces of the structure, the sensors of the probes are also aligned within the ring magnets.

To facilitate the coupling of the ultrasonic signal between the ultrasonic transducer of the driven probe and the structure, a couplant may be disposed between the ultrasonic transducers and the respective surfaces of the structure. While air or water jets may be used as a couplant, a driven probe may also include an inlet for fluid that is pumped between the ultrasonic transducer and the first surface of the structure. In this regard, the driven probe may include a housing in which the magnet and the ultrasonic transducer are disposed, and which defines the inlet. The housing may also define a fluid conduit to direct fluid flow from the inlet to a plurality of channels to disburse the flow of fluid between the probe and the first surface of the structure. A plurality of channels may be, for example, a series of radially directed recesses or a plurality of holes. The fluid conduit may be in fluid communication with that portion of the ultrasonic transducer of the driven probe that faces the first surface of the structure. Thus, the fluid that is pumped between the ultrasonic transducer and the first surface of the structure may facilitate coupling of the ultrasonic signals produced by the ultrasonic transducer into the structure. Likewise, the tracking probe may include an inlet for fluid that is pumped between the ultrasonic transducer of the tracking probe and the second surface of the structure. In this regard, the tracking probe can also include a housing in which the magnet and the ultrasonic transducer are disposed, and which defines the inlet. The housing may also define a fluid conduit to direct fluid flow from the inlet to a plurality of channels to disburse the flow of fluid between the probe and the first surface of the structure. The fluid conduit may be in fluid communication with that portion of the ultrasonic transducer of the tracking probe that faces the second surface of the structure. Thus, ultrasonic signals emerging from the structure may be effectively coupled to the ultrasonic transducer of the tracking probe by the fluid that is pumped therebetween. By pumping fluid between the ultrasonic transducers and the respective surfaces of the structure, water jets are not required such that the ultrasonic transducers of the driven and tracking probes may include arrays of ultrasonic transducers, thereby permitting the rate at which the structure is inspected to be increased and the associated inspection cost accordingly decreased.

A probe may include a bearing contact, such as a ball and socket bearing, a water bearing, or an air bearing, for contacting a surface of the structure, supporting or suspending the probe, maintaining orientation and spacing of the probe with respect to the surface, and reducing the frictional drag of the probe on the surface of the structure being inspected to permit smooth translation of the probe across the surface of the structure. Thus, the probe may translate along the surface of the structure. As such, the orientation of the probe relative to the surface of the structure and the spacing of the probe relative to the surface of the structure may be maintained by the contact between the probe and the surface of the structure without requiring the complex motion control systems used by conventional scanning systems. This independence from the motion control systems used by conventional scanning systems may further reduce the cost a probe and permits the probe to be moved in a controlled fashion over a surface of a structure that is relatively inaccessible for a robotic arm or other conventional motion control system. The driven and tracking probes may also use the water or pressurized air that is used for bearing contact as a couplant between a sensor, such as an ultrasonic sensor, and the surface of the structure being inspected. Fluid bearings and fluid coupling are described more fully below. However, the water or pressurized air that is used for bearing contact need not pass in front of the transducer to act as a couplant but may be used only between the probe and the surface of the structure, such as where holes or recesses of a fluid channel are disposed around the transducer of a probe. Other fluids, such as a gases, liquids, or gas-liquid mixtures, may be used as couplants and/or to provide a bearing contact between a probe and a surface being inspected. Rather than being supported by a fluid bearing, the probes may contact the surface of the structure using a ball and socket bearing. When using ball and socket bearings, a fluid, such as water or air, may be used as a couplant between an ultrasonic transducer of a probe and a surface of the structure, such as bubbling water from an inlet in a probe.

Figure 1A:
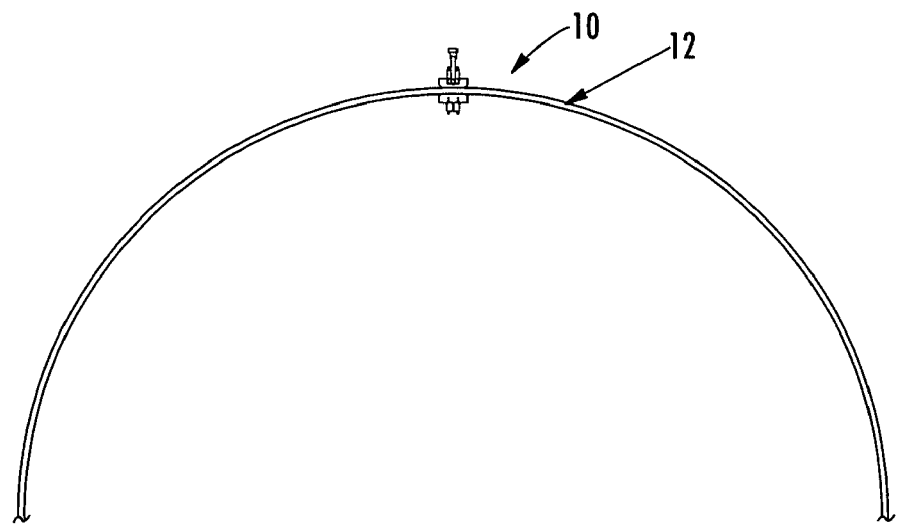
FIG. 1A is a schematic diagram of two probes of an apparatus magnetically coupled to surfaces of a structure for inspection.
Figure 1B:
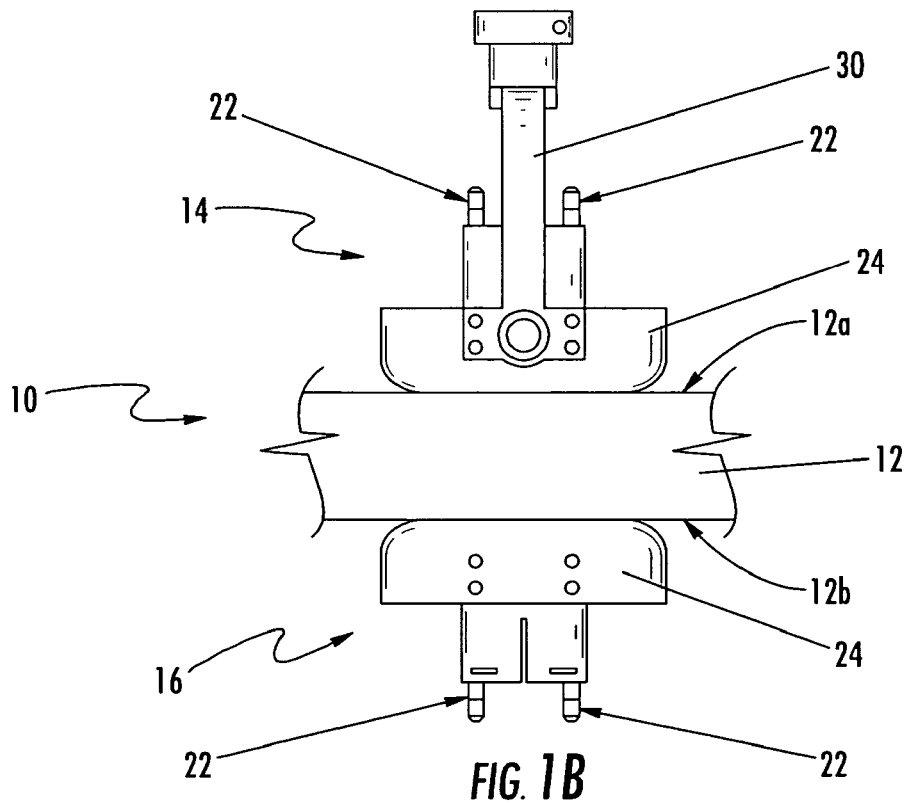
FIG. 1B is a magnified schematic diagram of two probes of an apparatus magnetically coupled to surfaces of a structure for inspection.
Figure 1C:
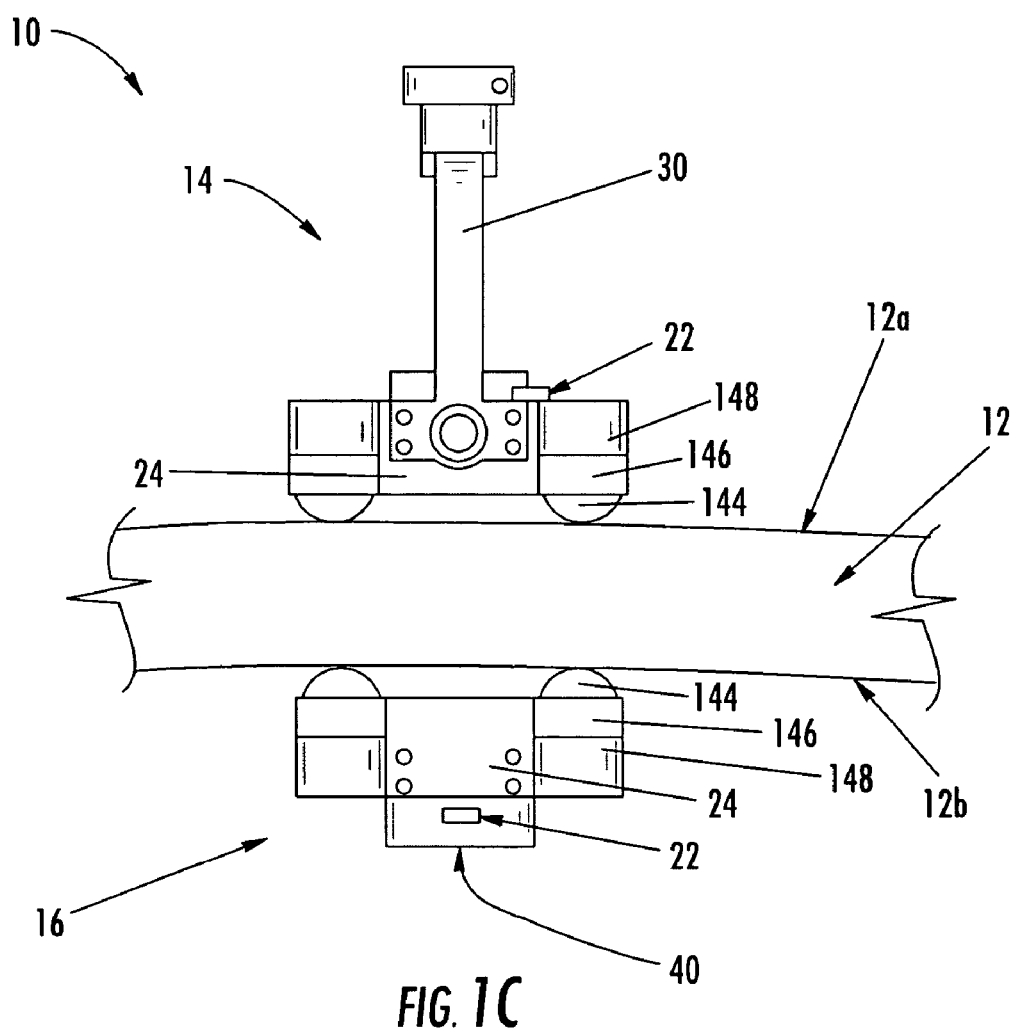
FIG. 1C is a magnified schematic diagram of two probes of an apparatus magnetically coupled to surfaces of a structure for inspection using ball bearing contact members.

Referring now to FIGS. 1A, 1B, and 1C, an apparatus 10 for inspecting a structure 12 is depicted. The apparatus 10 can inspect a variety of structures formed of various materials. Since the apparatus relies to some extent upon the establishment of magnetic fields through the structure, however, the structure is preferably non-magnetic, that is, the structure preferably has no magnetic permeability. Structures that may be inspected with an embodiment of an inspection device of the present invention may include, but are not limited to, composites, non-ferromagnetic metals (e.g. aluminum alloy, titanium alloy, or aluminum or titanium hybrid laminates such as GLARE or Ti/Gr), and polymers. It should be noted that the surfaces, and the material therebetween such as intermediate surfaces commonly referred to as septums, which collectively define the material through which the driven and tracking probes are magnetically coupled, preferably comprise a non-ferromagnetic material because the magnetic coupling between the probes would be diminished or eliminated by a ferromagnetic material located between the actuating portion and the inspecting portions.

While a portion of a relatively simple but large structural panel 12 is depicted during the course of an inspection in FIGS. 1A and 1B, a structure may be any myriad of shapes and/or sizes. In addition, the structure that is inspected may be used in a wide variety of applications, including in vehicular applications, such as in conjunction with aircraft, marine vehicles, automobiles, space craft and the like, as well as other non-vehicular applications, such as in conjunction with buildings and other construction projects. Moreover, the structure may be inspected prior to assembly or following assembly, as desired.

Figure 10:
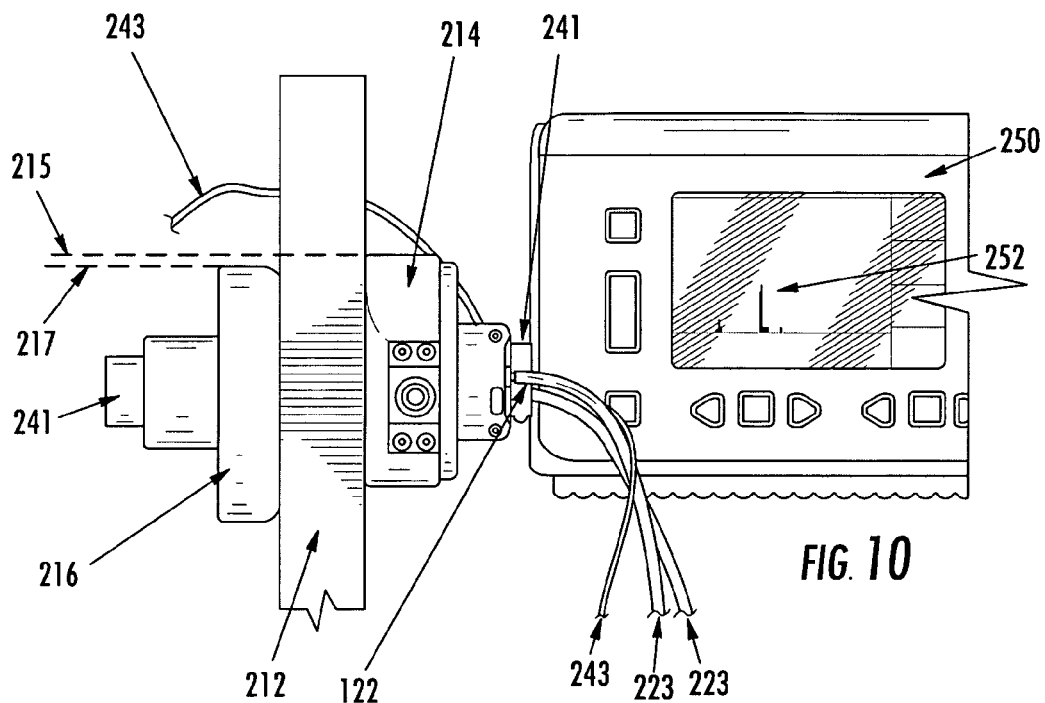
FIG. 10 is a side view of two water bearing probes positioned across a structure being inspected.

An inspection apparatus 10 may include a driven probe 14 disposed proximate a first surface 12a of the structure 12 and a tracking probe 16 disposed proximate an opposed second surface 12b of the structure. Embodiments of the present invention may also be used with an inspection device similar to that disclosed in U.S. Pat. No. 6,722,202 to Kennedy directed to magnetically attracted probes for inspection of a structure, which is incorporated by reference. The shape and size of an inspection probe, and housing thereof, which may employ the present invention is not limited to the specific embodiments describe and disclosed herein or in the U.S. Pat. No. 6,722,202 patent or referenced co-pending applications, but may be any shape or size capable of operating in accordance with the present invention. Driven and tracking probes are advantageously initially positioned in alignment so as to be directly opposed one another or otherwise in positional correspondence with one another, as shown in FIGS. 1A, 1B, and 10. As shown in FIGS. 1A, 1B, and 10, for example, this alignment provides a linear relationship between the probes 14, 16 such that one probe is preferably not translated or offset laterally across the surface of the structure 12 from the other probe. As described below, this positional relationship or correspondence between the driven and tracking probes is maintained as the probes are moved along the respective surfaces of the structure and any offset or translation may be corrected by an alignment compensator of an embodiment of the present invention.

Each probe 14, 16 includes a ring magnet 18, 118 that may be disposed within a housing 24, 124. The magnets of the probes magnetically attract the driven and tracking probes toward the respective surfaces of the structure 12. Using probes with ring magnets on opposing surfaces of a structure also aligns the two probes with respect to the other. By comparison, magnetically coupled inspecting probes using bar magnets, flat magnets, cylindrical magnets, and the like, require configurations of magnets and/or ferromagnetic materials to align the probes. Such configurations typically cannot provide the flexibility of ring magnets which may permit a tracking probe to rotate freely with respect to a magnetically coupled driven probe while maintaining alignment of ultrasonic transducers located within the center of the ring magnets in the driven and tracking probes. Magnetically coupled probes employing embodiments of the present invention may alternatively, or in addition, use magnets and/or ferromagnetic materials to provide alignment and/or magnetic attraction between probes. While each probe may include any number of magnets, each probe need only include one ring magnet which reduces the size, weight, cost, and complexity of the probes. Magnets of the illustrated probes may be ring magnets formed of neodymium iron boron, which have advantageously have greater magnetic flux (around 12,000 gauss) than standard ceramic or ferrite magnets (around 3,900 gauss). Further embodiments of inspection probes and alignment compensators of the present invention may include magnets of different material, such as Samarium Cobalt or Alnico and/or electromagnets or other magnetic coupling means. The term "magnet" as used herein is inclusive of electromagnets. Alignment compensators of the present invention and inspection probes may further comprise magnetic shunting mechanisms to control the magnetic flux of the magnetic couplings, a non-limiting example being rare earth metal switched magnetic devices disclosed in U.S. Pat. No. 6,180, 928. While various types of ring magnets may be used, the driven and tracking probes of one embodiment include permanent ring magnets, such as NdFeB ring magnets. The size of ring magnets for both the driven and tracking probes may be dependent, at least in part, upon the weight of the respective probes, the thickness of the structure undergoing inspection, and the material that forms the structure undergoing inspection. For example, a ring magnet of a probe may be 4 inches in diameter and 1 inch in height with a magnetic flux of 3.9k Gauss across the surface of the ring magnet if the magnet is a standard ferrite ring magnet or 12 k Gauss if the magnet is an NdFeB ring magnet. Additionally, driven and tracking probes may include ring magnets having either the same or different sizes.

Although ring magnets may be used independently to positionally align probes, rotational alignment of probes may be enhanced by incorporating at least one additional magnet or ferromagnetic material to at least one of the probes. For example, if one of the probes includes ferromagnetic material, such as a plug of ferromagnetic material, the other probe may include an additional magnet, or possibly an alignment compensator, positioned such that the probes are properly positioned with respect to one another when the ferromagnetic plug and the additional magnet are aligned since the ferromagnetic plug and the additional magnet of the other probe will be attracted to one another when these elements are properly aligned to position the probes with rotational alignment. Similarly, if the probes each include two additional magnets, where the two additional magnets of each probe have opposite polarities, when the probes are misaligned, the additional magnets of the probes would be repelled and produce a rotation of the probes until the additional magnets of the probes align with the additional magnets of the other probe that are of the opposite polarity. As such, these types of additional magnets and ferromagnetic materials may be used as rotational alignment keys for probes.

In determining the type of magnets, the weight of the magnets, the surface area of the magnets and the increased demagnetization effects attributable to the cylindrical length to diameter ratio and/or cylindrical length to radial width ratio of the magnet are typically taken into consideration. In this regard, magnets that are relatively thin and flat may have a substantial surface area so as to generate significant magnetic flux. However, these magnets are generally inefficient since they suffer from increased demagnetization effects due to their relatively small cylindrical length to diameter ratio and/or cylindrical length to radial width ratio relative to thicker, more rod-like ring magnets having a smaller surface area.

At least one of the probes 14, 16, usually the driven probe, includes a sensing element 32, 132 for inspecting the structure 12 as the probe is moved over the respective surface of the structure. Further with respect to FIGS. 2A, 2B, 3, and 4, the sensing element 32, 132 is positioned in the ring magnet 18, 118 within a central cavity 40, 140 of a housing 24, 124 A sensing element may be a camera, an x-ray detector, pulse echo sensor, or the like, but generally is an ultrasonic transducer, such an ultrasonic transmitter and/or an ultrasonic receiver. For example, the ultrasonic transducer may be a 1 MHz immersion transducer from Agfa/Krautkramer of Lewistown, Pa.

Such probes provide for through transmission ultrasonic (TTU) inspection. Ultrasonic signals are transmitted into the structure by the ultrasonic transducer of one probe and received by the ultrasonic transducer of the other probe to detect flaws, including cracks, voids and/or porosity. However, only one probe needs to include a sensing element 32, 132 for inspection from one side of the structure 12, such as for pulse echo (PE) inspection.

To facilitate the coupling of ultrasonic signals between ultrasonic transducer(s) of the driven and/or tracking probes 14, 16 and the structure 12, a couplant may be used. While air or water jets may be used as a couplant, the driven and/or tracking probes 14, 16 and, in particular, the respective housings may include an inlet 22, 122 for fluid such as water or air, that is pumped between an ultrasonic transducer and a respective surface 12a, 12b of the structure.

As shown in FIGS. 2A, 2B, 3, and 4, the housing 24 includes a fluid conduit 23 connecting the fluid inlets 22 to fluid dispersion channels 42, such as recesses or holes. The fluid conduit 23 and/or the fluid dispersion channels 42 may also be in fluid communication with a portion of the sensing element 32, such as an ultrasonic transducer, that faces a surface of the structure 12 proximate the probe. The sensing element 32, such as an ultrasonic transducer, may be recessed within the housing 24. Thus, fluid that is introduced through the inlet 22 flows through the fluid conduit 23, including an internal channel, defined by the housing 24 and effectively fills the gap between the ultrasonic transducer and the surface of the structure 12. Advantageously, the fluid flows smoothly over and between the ultrasonic transducer and the surface of the structure with no bubbles, cavitation or turbulence that could otherwise detrimentally affect the signal to noise ratio.

The fluid is supplied from a reservoir connected to the inlet 22. A tube press fit around the inlet 22 leads to a flow control valve, which may include a bleed value to maintain constant pressure and prevent excess pressure or volume of fluid.

Figure 2A:
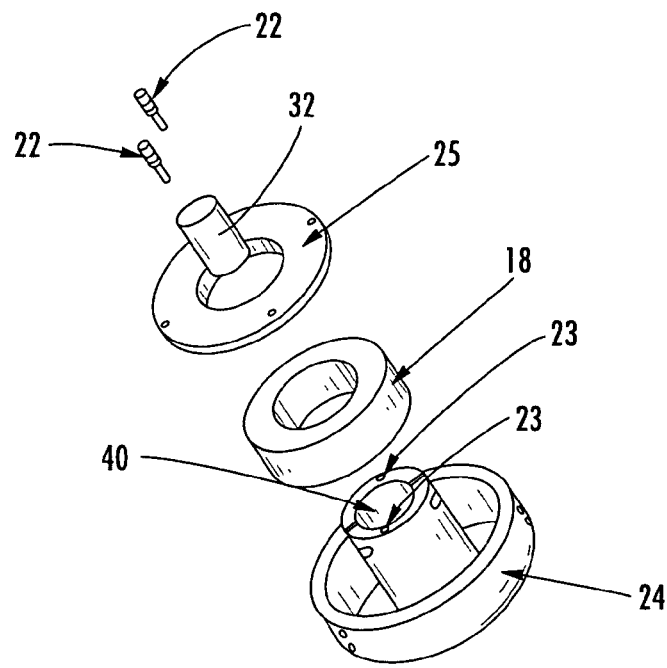
FIG. 2A is an exploded view of a probe.
Figure 2B:
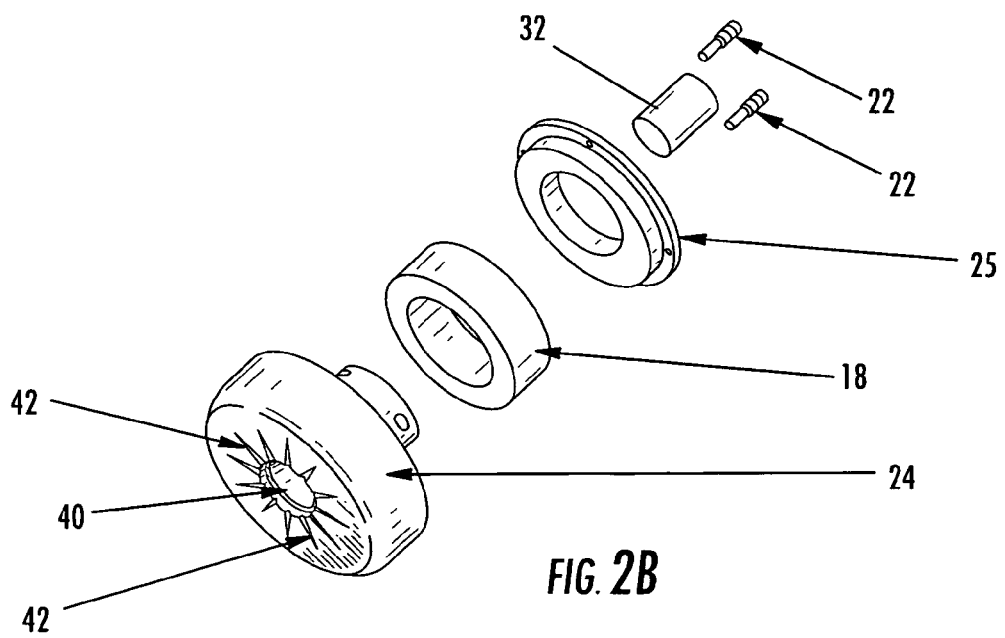
FIG. 2B is yet another exploded view of the probe.
Figure 3:
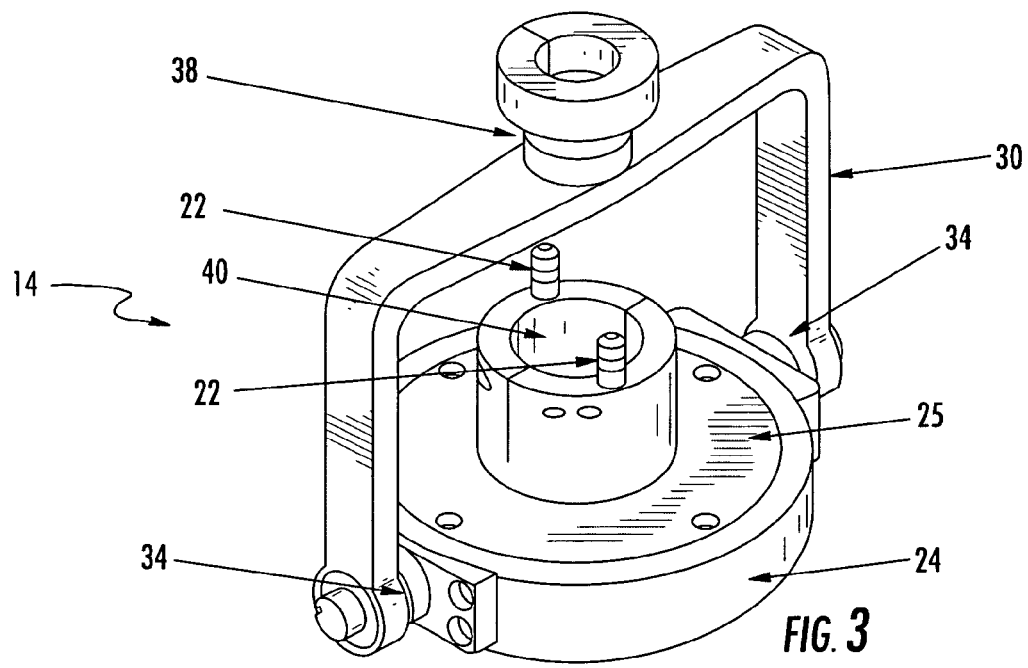
FIG. 3 is an overhead perspective view of a probe.
Figure 4:
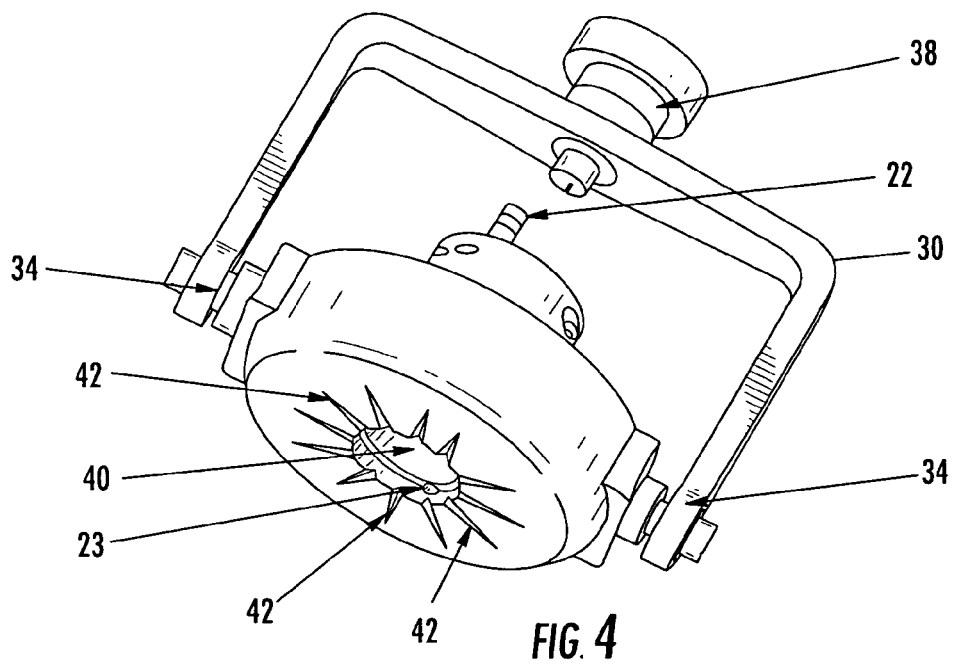
FIG. 4 is a bottom perspective view of the probe.
Figure 5A:
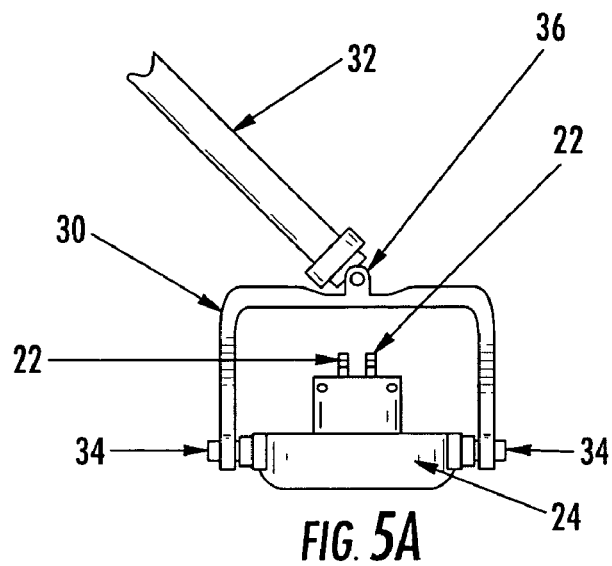
FIG. 5A is a side perspective view of a probe including a yoke attachment.
Figure 5B:
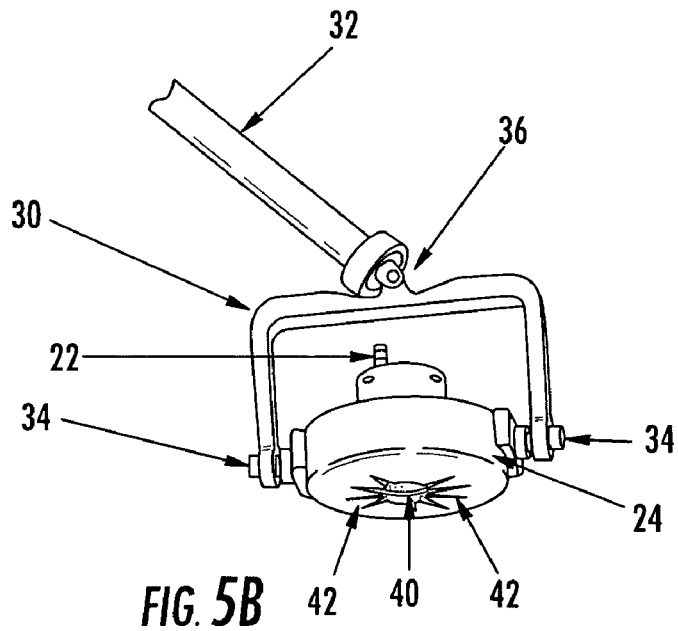
FIG. 5B is a bottom perspective view of the probe including a yoke attachment.
Figure 5C:
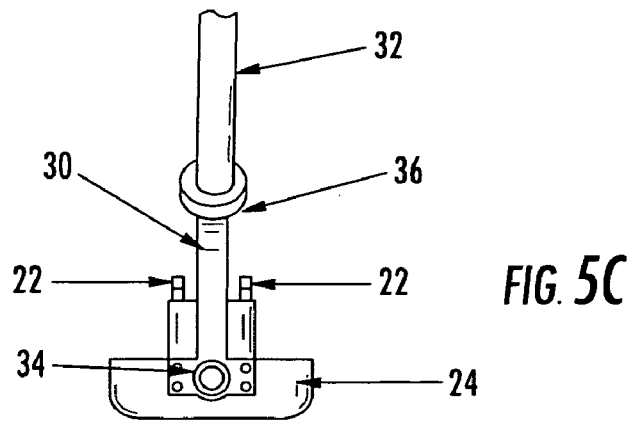
FIG. 5C is yet another side perspective view of the probe including a yoke attachment.

As shown in FIGS. 2A and 2B, a cap 25 secures the ring magnet 18 into a cup formed in the housing 24. The bottom of the housing 24 may also include channels 42 to direct the flow of fluid to create a fluid bearing. If the fluid is also used as a couplant, the fluid passes over an sensing element 32, such as an ultrasonic transceiver, affixed within the central cavity 40 of the housing 24, and out through the channels. The shape and size of the housing does not dictate the present invention, but may be adapted to incorporate or facilitate features of the present invention. For example, the shape and size of the housing 24 shown in FIGS. 2A and 2B are dictated to provide support for the ring magnet 18 and fluid inlets 22. The shape is further dictated to provide smooth edges which may be proximate a surface of a part to avoid the housing interfering with the operation of embodiments of the present invention.

A handle or other connector, such as a yoke attachment 30, is used for controlling a driven probe 14 across a surface of a part. FIGS. 5A, 5B, 5C, and 9 show a yoke attachment 30 for a manual, semi-automatic, or robotic arm extension.

In operation, the driven and tracking probes 14, 16 are disposed proximate first and second surfaces 12a, 12b of the structure 12. As shown in FIGS. 1A, 1B, and 1C the driven and tracking probes may advantageously be disposed in contact or bearing contact with the structure. Bearing contact may provide suspension of a probe above a surface of a structure, such as by a fluid bearing and/or a ball and socket bearing. For example, a water bearing or an air bearing may support a probe on a structure. To facilitate contact of the probes with the respective surfaces of the structure and to avoid any undesirable damage or other marring of the respective surfaces of the structure as the result of contact with the probes, the driven and tracking probes can each also include at least one contact member 28, such as a ball and socket bearing or a skid, which can be used in conjunction with or independently from a fluid bearing. Skids may be beneficial for fluid bearing probes such as to prevent damage or marring of a surface of a structure under test when initially placing a probe on the structure or magnetically coupling two probes on opposite sides of the part, particularly when the fluid bearing may not be in use, such as before fluid is provided to the probe or after fluid is stopped flowing to the probe. Alternatively, a probe may include one or more ball and socket bearings that contact the respective surface of the structure and that permit the probe to ride therealong when not using a fluid bearing. Fluid bearings, such as water bearing and air bearings, and ball bearings may be used to maintain the spacing and orientation of the probes. Water, air, or ball bearings may be used to reduce the fiction between the inspection probe and the surface of the structure under inspection, such as to displace the probe from contacting the surface of the structure using hydraulic or pneumatic flotation or a hydrostatic bearing. Further, use of bearing contact between the inspection probe and the surface of the structure may prevent scratching of soft skins or denting of panels of the skins. Use of bearing contact may also provide smooth translation of an inspection probe over the surface of a structure to allow an inspection probe to maintain an intended direction, maintain alignment of transducers and/or receivers in inspection probes, and allow continuous scanning of a surface regardless of size, smoothness, or flatness of the surface.

A fluid bearing, also referred to as a fluid dynamic bearing, may be created by pumping a thin layer of fluid between the surface of a housing for a probe which is adjacent to the part under inspection and the surface of the part adjacent to the probe. The pressure from the magnetic attraction of the probe towards the part on the fluid and the pumping of the fluid into the compressed space creates the fluid bearing. The housing for the probe rests upon the thin layer of fluid between the probe and the surface of the part. Although fluid bearings typically use a seal to maintain hydrostatic fluid in a defined space, pumping fluid into the space for the fluid bearing at the rate that the fluid escapes from the fluid bearing maintains sufficient volume and pressure of fluid in the space to achieve a fluid bearing. As described herein, a fluid used for a fluid bearing may also be used to provide a couplant between a sensor and a surface of the part under inspection. For example, the water of a water bearing may flow between the transmitting end of an ultrasonic transducer and the adjacent surface of the part under inspection and then may flow between a surface of the housing for the probe and an adjacent surface of the part under inspection to produce a fluid bearing.

Figure 6:
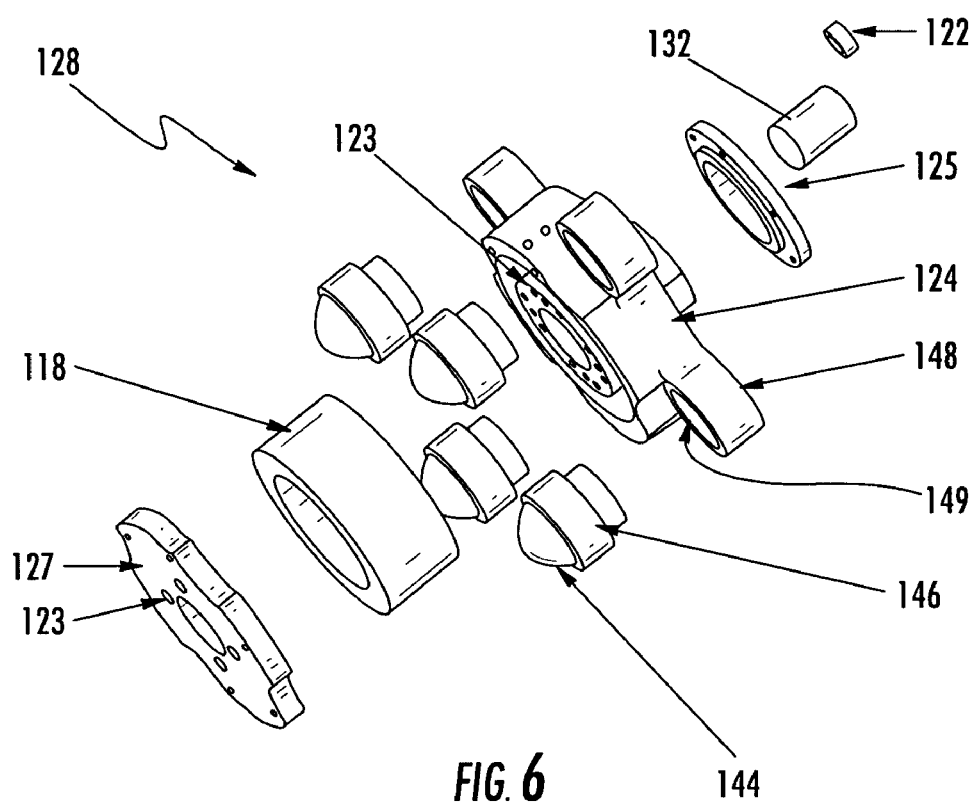
FIG. 6 is an exploded view of a probe including ball and socket contact members.

FIG. 6 is a bottom perspective view of an exploded diagram of a probe including ball and socket bearings. A housing 124 may include a central cavity 140 to retain a sensor 132 such as an ultrasonic transducer. By comparison to the embodiment of FIG. 2B, the embodiment of FIG. 6 has an inverted, compressed housing 124, disposed around a ring magnet 118, with two caps 125, 127 and ball and socket bearings 128. Alternatively, a ring magnet may be retained in a housing with a cap integrally formed by the housing or with a recess for the ring magnet such that the housing does not require a cap or caps to retain the ring magnet. The ball and socket bearings 128 may include spherical bearings 144 each housed by a socket 146. The sockets 146 may be attached to the housing in ball and socket support members 148 or may be integrally connected to and formed by the housing. In one embodiment, three or more spherical ball are held in corresponding sockets to facilitate the rolling inspection of two magnetically attracted probes on opposite surfaces of a structure.

Figure 7:
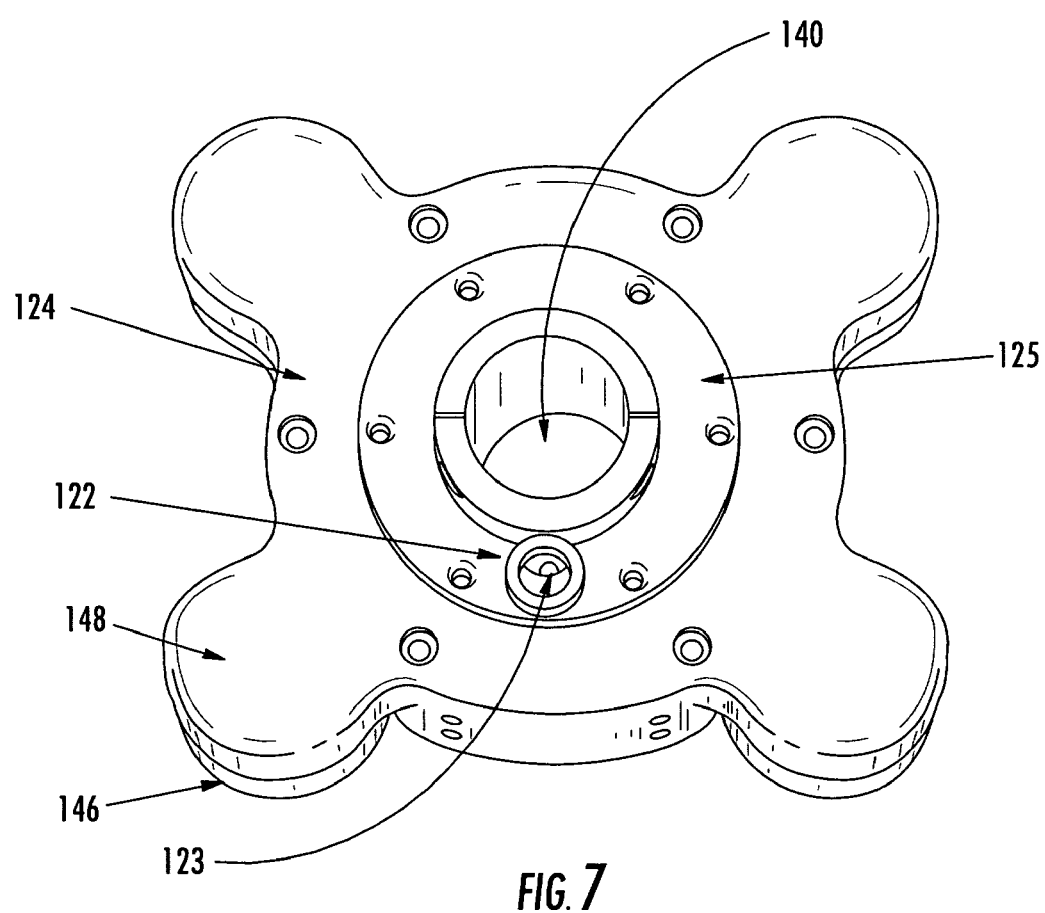
FIG. 7 is a top plan view of a probe.
Figure 8:
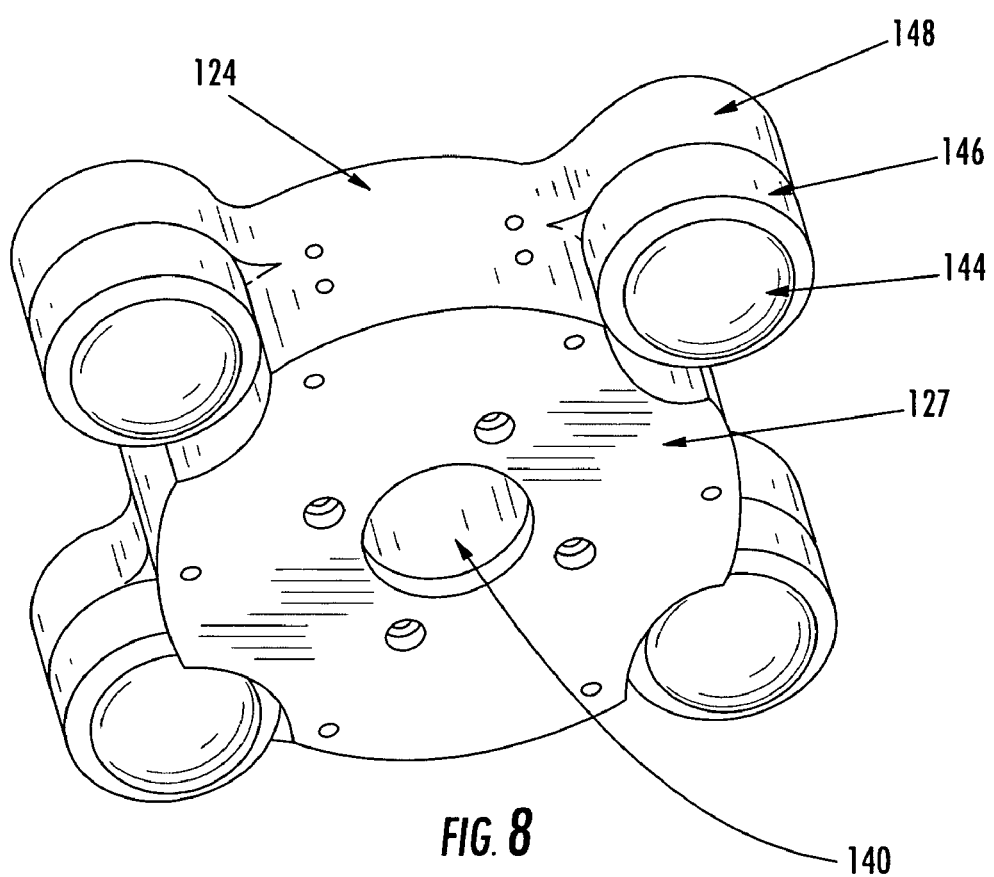
FIG. 8 is a bottom perspective view of the probe.

FIG. 7 is a top plan view of a probe. FIG. 8 is a bottom perspective view of a probe. The housing 124 defines a central cavity 140 in which a sensor 132 such as an ultrasonic transducer is disposed. The housing 124 also includes an outer perimeter in which the sockets 146 are integrally formed and into which respective balls 144 are inserted. Between the outer perimeter and central collar of the housing 124 is disposed a ring magnet. A first cap 125 and a second cap 127 retain and/or secure the ring magnet within the housing 124. A fluid inlet 122 may be attached to, disposed in, or otherwise formed by the housing to permit the flow of fluid through the inlet and the housing. In a ball bearing embodiment, fluid such as water may be used as a couplant between an ultrasonic transducer and the surface of the structure being inspected. An inlet 122 may be part of a fluid conduit 123 that permits the flow of fluid through the housing 124.

Figure 9:
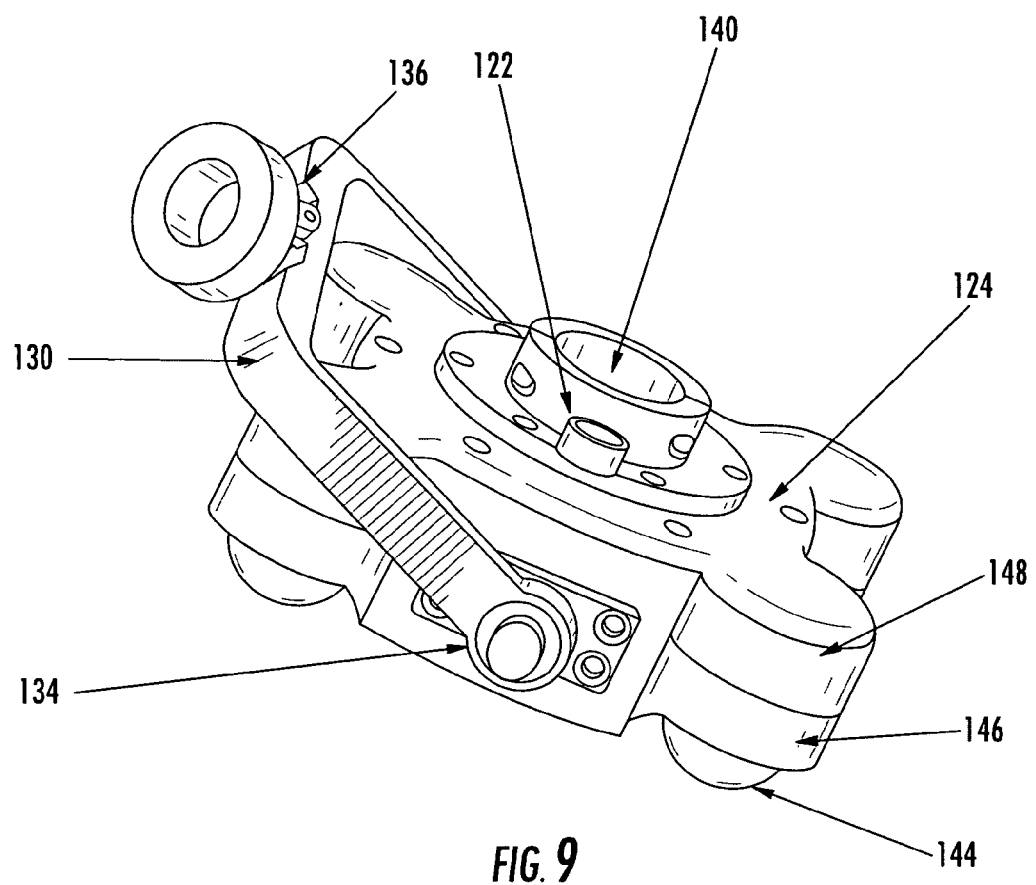
FIG. 9 is an overhead perspective view of a probe including a yoke attachment.

FIG. 9 is an overhead perspective view of a probe including a yoke attachment. The probe may include, or have attached, a handle or other connector, such as a yoke attachment 130, for controlling and driving the probe across a surface of a part.

By permitting contact or bearing contact between the driven and tracking probes 14, 16 and the respective surfaces 12a, 12b of the structure 12, and by the magnetic attraction between the ring magnets of the probes, the position and orientation of the probes and, more particularly, the sensing elements, such as the ultrasonic transducers, of the probes may generally be maintained without requiring a complex motion control system or other type of positioning system. Additionally, the contact or bearing contact between the driven and tracking probes and the respective surfaces of the structure may maintain a consistent spacing between the respective sensing elements, such as the respective ultrasonic transducers, and the structure, without requiring complex motion control systems or other positioning systems. Further, the use of magnetically attracted inspection probes permits continuous scanning techniques such as manual scanning of an entire surface by comparison to point-by-point or grid-type inspection methods that may commonly be used for manual, semi-automated, and automated scanning systems. Because magnetically attracted probes preferably maintain positioning of the transducers, an inspection area may be as large as the entire structure, and a single operator may be able to inspect the structure.

The operation of the apparatus 10 is described in conjunction with driven and tracking probes 14, 16 configured to conduct a through transmission ultrasonic inspection. However, the driven and tracking probes may be used in other manners as described below. By way of example of the operation of one embodiment of the driven and tracking probes, however, the driven and tracking probes are disposed proximate to and generally in contact with the opposed first and second surfaces 12a, 12b of a structure 12 while maintaining position and magnetic attraction between the probes. Fluid, such as water, may then be bubbled through the inlet 22 of each probe and between the ultrasonic transducers and the respective surfaces 12a, 12b of the structure 12. Bearing contact, such as a fluid bearing, including liquid and air bearings, or ball bearings may be used to maintain adequate spacing between the probe and the surface of the part under inspection. In such a manner, the bearing contact may be used to prevent the probe from contacting and possibly damaging the surface of the part. Further, the bearing contact provides the probe the ability to translate along the surface of the part for continuous scanning. The ultrasonic transducers are activated such that the ultrasonic transducer of one probe, emits ultrasonic signals into the structure. A drive element, such as a voltage or current source connected to a computerized control program, is generally associated with the ultrasonic transducer of the driven probe so as to actuate the ultrasonic transducer to emit the ultrasonic signals. This drive element may be co-located with the driven probe or may be remote therefrom and electrically connected to the ultrasonic transducer. Correspondingly, the ultrasonic transducer of the other probe, receives the ultrasonic signals originally transmitted by the ultrasonic transducer of the driven probe following the propagation of the ultrasonic signals through the structure.

While the ultrasonic signals are transmitted through the structure 12 and fluid is passed over the respective ultrasonic transducers, the driven probe 14 is moved along the first surface 12a of the structure. While the motive force required to move the driven probe along the first surface of the structure may be applied in various manners, the driven probe of the illustrated embodiment includes a handle that may be engaged by a robotic arm or the like. As known to those skilled in the art, the robotic arm can be controlled by a motion control system or other positioning system so as to controllably move the driven probe in a predefined manner and in accordance with a defined pattern along the first surface of the structure.

As a result of the magnetic attraction established between the driven and tracking probes 14, 16 and, more particularly, between the magnets 18, 118 of the driven and tracking 14, 16 probes, the tracking probe 16 follows the driven probe 14. Thus, the tracking probe 16 moves so as to remain in a preferably aligned, opposed position relative to the driven probe 14. Accordingly, the tracking probe 16 can be disposed proximate to and can ride along a second surface 12b of a structure that may be relatively inaccessible, such as the interior of a cylindrical structure or other structure having a closed shape.

By passing fluid between the ultrasonic transducer and the respective surface of the structure 12, the ultrasonic signals are effectively coupled into and/or out of the structure.

Moreover, while a single ultrasonic transducer is depicted in FIGS. 2A, 2B, and 6, driven and/or tracking probes 14, 16 may include an array of ultrasonic transducers to increase the inspection area since the coupling provided by the fluid permits inspection in an ultrasonic array mode, thereby increasing the speed with which the inspection is performed and potentially reducing the cost associated with the inspection.

A tracking probe may include a larger diameter transducer than the transducer of a driven probe. Using a larger tracking probe transducer enables a more uniform signal over a larger area than would a corresponding smaller transducer. Thus, using a larger transducer in the tracking probe may minimize the effect of small misalignments between the driven probe and tracking probe, and transducers thereof, such as misalignments due to discontinuities in the surfaces of the structure, positional lagging of the tracking head, and gravitational offset.

II. Alignment Compensation

The driven and tracking probes may be misaligned or translationally offset for reasons such as discontinuities in the surface of the structure, positional lagging of the tracking head, and gravitational offset of the tracking head. For example, when probes are in a vertical or near-vertical position with respect to a gravitational force, the weight of the tracking probe of the magnetically coupled devices may cause the tracking probe to hang down relative to the driven probe. In this instance, the magnetic coupling is not strong enough to hold the centers of the driven and tracking probes perfectly aligned. When transducers of driven and tracking probes are misaligned, the signal transmitted through a part under inspection and received by a receiving probe, typically the tracking probe, may be diminished. When scanning in horizontal or near-horizontal positions with respect to a gravitational force, the probes may be aligned with acceptable accuracy for a strong signal to be transmitted from one probe, propagate through the part under inspection, and be received by the other probe. Further, for example, at higher scanning speeds, a tracking probe may lag behind the driven probe due to the strength of magnetic coupling and frictional forces, causing transducer misalignment between the probes.

One option to account for misalignments between driven and tracking probes as described, may be to provide a larger transducer area in one of the probes, typically the tracking probe, to provide a greater area to receive a signal from a transmitting probe. Another possibility to account for misalignments may be to mount one of the transducers off-center. For example, in the case of a gravity-driven misalignment, the driven probe may have its transducer lowered relative to the transducer of the tracking probe to be in alignment with the transducer of a tracking probe. Similarly, at higher scanning speeds, the transducer of the driven probe may be moved in the trailing direction until it is aligned with the transducer of the tracking probe. However, adapting the position of a transducer may limit scan capabilities such that data may only be taken in one scan direction or one orientation, or the off-center mounting of a transducer to be made adjustable to account for different scan angles and speeds although the design of the probes would become more complex. Alternatively, or in addition, a tracking probe advantageously includes an alignment compensator of an embodiment of the present invention to correct misalignments between the tracking probe and the driven probe. For example, an embodiment of an alignment compensator of the present invention may compensate for off-centering and/or lagging of magnetically coupled devices caused by gravity or rapid movement of a driven probe.

FIG. 10 is a side view of two water-bearing probes positioned across a structure being inspected. As can be seen by the probes 214, 216 magnetic coupled on opposing sides of a structure 212 under inspection, the tracking probe 216 hangs lower than the driven probe 214 because the magnetic coupling between the driven probe 214 and the tracking probe 216 does not compensate or counteract the force of gravity on the tracking probe 216. Specifically, the top of the driven probe 214 is marked by a line 215 which is higher than the top of the tracking probe 216 which is marked by a lower line 217. In one embodiment, the probes 214, 216 in FIG. 10 have as much as a ⅜ inch vertical difference between the tops of the probes, respectively, although this offset will vary based upon the weight of the probes, the strength of the magnets, etc. As a result, the ultrasonic signal is attenuated by the offset in passing between the transducers 241 of the probes 214, 216. The result can be seen as a partial or low signal 252 due to the off-centering of the probes.

Figure 11:
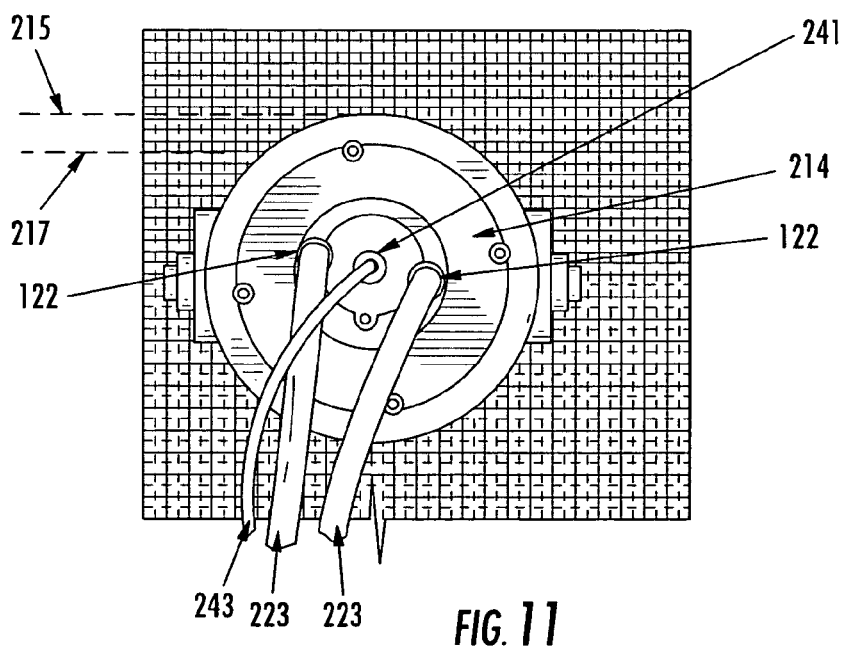
FIG. 11 is an orthogonal side view of the two water bearing probes positioned across the structure being inspected.

FIG. 11 is an orthogonal side view of the two water-bearing probes in FIG. 10. By comparison to the view shown in FIG. 10, the probe 214 which is visible in FIG. 11 is the driven probe 214. The tracking probe is behind the structure 212 under inspection. The top of the driven probe 214 is indicated by a line 215 by comparison to a lower line 217 which marks the top of the tracking probe 216.

Figure 12:
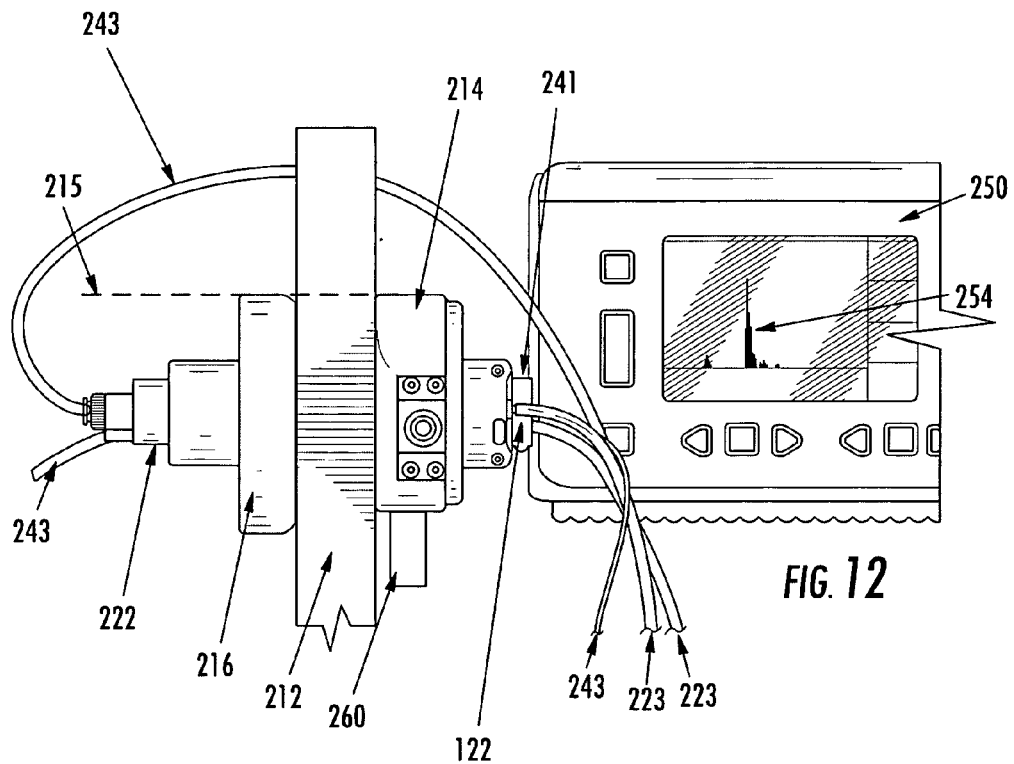
FIG. 12 is a side view of two water bearing probes and an alignment compensator according to the present invention.

FIG. 12 is a side view of two water-bearing probes and an alignment compensator according to the present invention. Unlike the probes 214, 216 in FIGS. 10 and 11, the probes 214, 216 in FIG. 12 are aligned with the tops of the probes at the same height indicated by a line 215. An alignment compensator 260 has been added to the driven probe 214 to force the tracking probe 216 up to align with the driven probe 214. Accordingly, an improved signal 254 may be acquired between the transducers 241 of the probes 214, 216.

Figure 13:
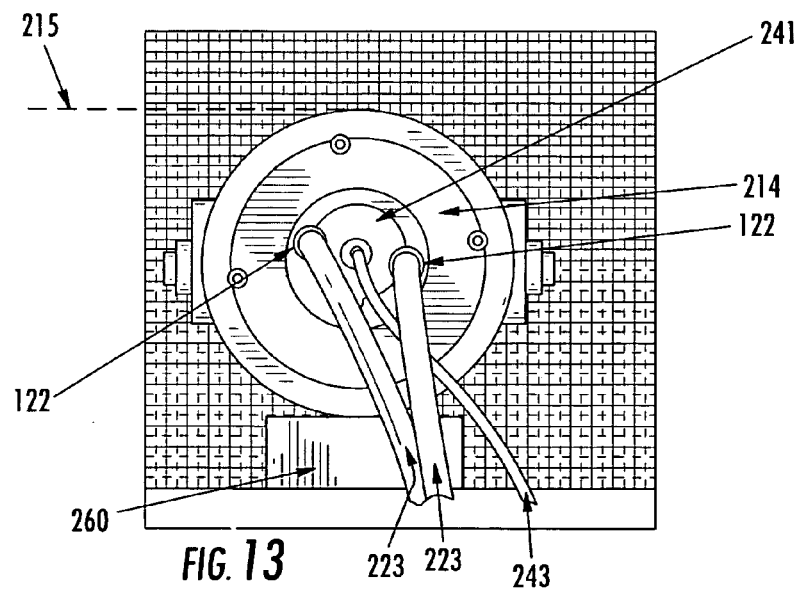
FIG. 13 is an orthogonal side view of the two water bearing probes and the alignment compensator.

FIG. 13 is an orthogonal side view of the two water-bearing probes and the alignment compensator. FIG. 13 relates to FIG. 12 as FIG. 11 relates to FIG. 10. The alignment compensator operates to raise or push up the tracking probe 216 to align the driven probe 214 and the tracking probe 216 such that the tops of both of the probes 214, 216 are aligned as indicated by a single line 215.

An alignment compensator of the present invention may be a permanent magnet or an electromagnet which modifies the magnetic field between the two opposing probes or, more particularly, between the two ring magnets of the opposing probes. Ring magnets used to produce the magnetic coupling between the probes have approximately uniform magnetic field strengths across their flat faces, referring to the respective surfaces of the ring magnets adjacent to the opposing sides of the structure against which the probes are respectively supported. As describe below, an alignment compensator according to the present invention may produce an opposing magnetic field relative to the face of the ring magnet of the driven probe. By way of example, with respect to the driven 214 and tracking 216 probes of FIG. 12 in which the tracking probe would otherwise be displaced downwardly with respect to the driven probe, the alignment compensator 260 is located on the lower side of the ring magnet of the driven probe 214 to push or oppose the magnetic field created by the lower portion of the ring magnet of the driven probe 214, that is, the portion of the ring magnet proximate the alignment compensator, thereby reducing the effective field strength resulting from the lower portion of the ring magnet of the driven probe. As such, the ring magnet of the tracking probe 216 will be more greatly attracted towards the upper portion of the ring magnet of the driven probe 214, thereby overcoming the tendency of the tracking probe to otherwise be displaced downwardly relative to the driven probe. In this embodiment, the magnetic field strength of the magnet of the alignment compensator 260 creates a force which pushes the tracking probe away from the alignment compensator, or more particularly, opposes the strength of the portion of the ring magnet of the driven probe 214 adjacent to the alignment compensator 260. Because the magnet of the alignment compensator 260 is positioned on a side or outside of the ring magnet of the driven probe 214, and as a result of the attractive force of the ring magnets, the ring magnet of the tracking probe 216, and correspondingly the tracking probe 216 itself, moves parallel to the ring magnet of the driven probe 214, and does not lift off or separate from the surface of the part under inspection.

Figure 14:
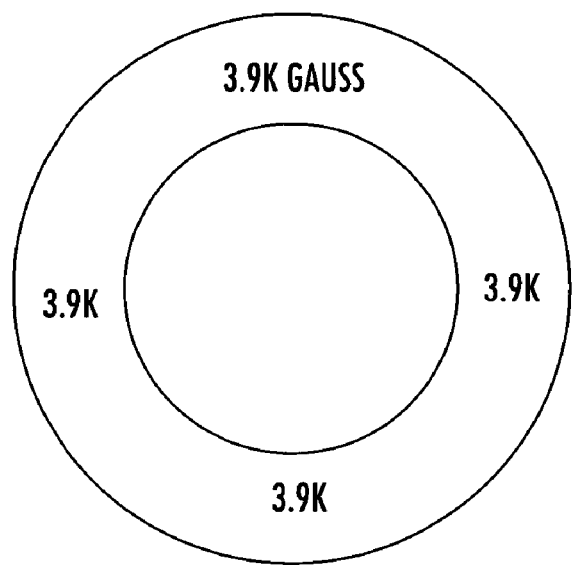
FIG. 14 is a diagram of a ring magnet.

FIG. 14 is a diagram of a ring magnet. The diagram in FIG. 14 shows, as a non-limiting example, the measured magnetic fields, using a directional gauss meter, on the surface of the ring magnet of a driven probe which would be adjacent to a surface of a structure under inspection. At the surface of the ring magnet, 3.9k gauss is uniformly recorded around the circumference of the surface of the ring magnet. The magnetic field strength is measured at approximately 90% of the surface field strength at one inch in front of the surface of the ring magnet.

Figure 15:
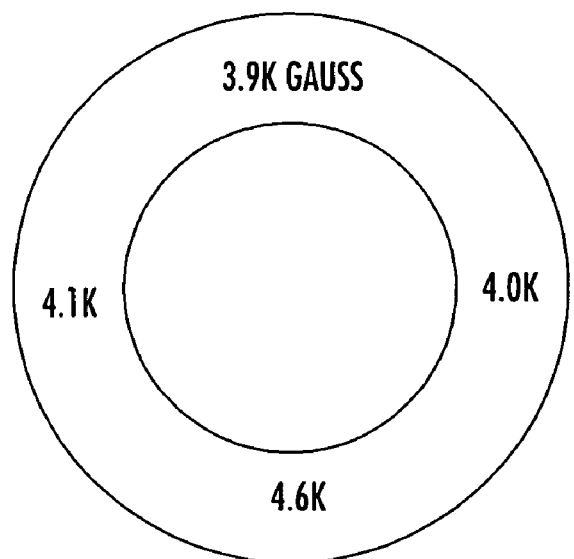
FIG. 15 is a diagram of the ring magnet and an alignment compensator.

FIG. 15 is a diagram of the ring magnet and an alignment compensator of the present invention. The presence of the magnet of the alignment compensator provides a field, represented by negative field strength numbers, which opposes the field strength of the ring magnet. The magnetic force of the magnet of the alignment compensator tends to lift or push, as the situation may be, the ring magnet of the tracking probe relative to the ring magnet of the driven probe. In a vertical position, the alignment compensator of this embodiment would generally be disposed lower than the ring magnet and would therefore lift the tracking probe. In a horizontal position with rapid scanning, the alignment compensator of this embodiment would generally be displaced in the trailing direction from the ring magnet and would accordingly push the tracking probe forward to match the velocity of the driven probe. Magnetic field strengths recorded at the surface of the alignment compensator coplanar with the surface of the ring magnet are approximately 3.8k gauss to 4.4k gauss. The negative measurement numbers represents an opposite magnetic force as that of the ring magnet.

As described, the magnet of an alignment compensator may be a permanent magnet or an electromagnet. If the magnet of an alignment compensator is an electromagnet, adjusting the electric current through the electromagnet will modify the strength of the alignment compensator, allowing centering adjustment of driven and tracking probes for scanning at various angles and/or various speeds. As described below, the probe of this aspect of the present invention may include an alignment sensor used to control the magnetic field generated by the electromagnet of the alignment compensator. For single orientation, constant angle scans and single orientation, fixed velocity scans, a permanent magnet may be used in an alignment compensator to simplify the components and operation of an alignment compensator. Further, in different applications or different scanning situations, a permanent magnet or an electromagnet of an alignment compensator may be changed for a different magnet such as when the scanning angle or scanning velocity changes. An alignment magnet housing may be used to support and/or retain different permanent magnets or electromagnets of an alignment compensator.

FIG. 16A is a schematic diagram of an embodiment of a probe with a ring magnet, an alignment compensator with two electromagnets on opposite sides of the ring magnet and an alignment sensor. FIG. 16B is a schematic diagram of an embodiment of an apparatus with two probes, each with a ring magnet, where one probe has an alignment compensator with two electromagnets and an alignment sensor, or motion and/or directional sensor, positioned across the structure being inspected. The arrangements or systems presented in FIGS. 16A and 16B may be advantageously useful in high-rate inspection situations where the alignment compensator may be used to correct misalignments between the driven probe and the tracking probe. For example, an alignment sensor, such as a linear encoder 270 or other directional sensor, may be used to identify the speed of the driven probe and possibly also the direction of movement of the driven probe. At low scan speeds, no compensation may be necessary for the alignment, or more specifically the misalignment, between a driven probe and a tracking probe and, as such, the electromagnets are not energized. However, for high-rate inspections, there may be sufficient lag such as caused by frictional and/or inertial drag on the tracking probe to produce a noticeable lag of the tracking probe, thereby decreasing the received inspection signal. Thus, for high-rate inspections, an alignment compensator system may be used to prevent tracking probe lag, such as by placing electromagnets of an alignment compensator on opposing sides of the ring magnet of the driven probe. The driven probe may include, in addition to the ring magnet 218, two electromagnets 262 which may be independently operated to provide correctional alignment between the driven probe and a tracking probe. The electromagnets 262 may be placed on the forward and trailing directional sides of the ring magnet 218. Depending upon the particular direction of motion, these electromagnets 262 of the alignment compensator system may be powered to push the tracking probe to keep up with the driven probe. For example, although preferably the scanning would be performed in the forward or trailing directions, the electromagnets may be powered at varying amounts using a variable power supply to control misalignments of the driven and tracking probes along directions not coordinated with the forward and trailing positions of the electromagnets 262 of the alignment compensator system. Additional electromagnets 262 may be positioned at various other locations around a ring magnet 218 of the driven probe to provide for additional correction between driven and tracking probes moving in any number of directions. By way of example, a signal sensor of an alignment compensator system may monitor the TTU signal that is transmitted through the part and communicate with a controller to adjust a variable power supply to alter the performance of an alignment compensator based upon the measured TTU signal, such as to adjust the correction by the alignment compensator to improve the signal strength, to increase the measured signal by correcting misalignments between driven and tracking probes. For example, if a signal sensor of an alignment compensator system identifies that the signal strength is reduced in a manner inconsistent with attenuation due to a flaw in the structure, the signal sensor may indicate to the controller, in coordination with an alignment sensor such as a linear encoder, to increase or decrease the power to an electromagnet to correct for misalignment between driven and tracking probes. Similarly, a magnetic indexing system such as disclosed in co-pending application entitled "Control System and Method for Magnetic Indexer for High Accuracy Hole Drilling," published on Nov. 12, 2003, as U.S. Patent Appl. Pub. No. 2003/0210027, the contents of which are incorporated by reference in its entirety, including, but not limited to, the disclosure of sensing a magnetic or ferromagnetic material through a structure, may be used by a controller of an alignment compensating system for aligning magnetically coupled probes using an alignment compensator of the present invention. Where an alignment compensator includes more than one electromagnet, a controller may turn off the power of one or more of the electromagnets to adjust the performance of the alignment compensator.

The alignment sensor may be a linear encoder 270, an optical sensor, directional sensor, or wheel encoder that is mounted to the control head to provide instantaneous direction and/or speed information which may be used by the controller 268 to modify and adjust the power of electromagnets 262 in an alignment compensator system. Information from the alignment sensor may be provided to an encoder/decoder 266, also referred to simply as a decoder, which defines data transmitted to a controller 268 which adjusts and modifies the power of the electromagnets 262, and, thus, the alignment compensator, by controlling the power supply 264 for the electromagnets 262. For example, as a driven probe moves in a forward direction, the alignment sensor may identify the forward motion of the driven probe and provide the information to the decoder 266 which may provide data to the controller 268 to allow the controller 268 to adjust the power supply in the electromagnets 262 to decrease the power to the forward electromagnet in the alignment compensator system and increase the power to the trailing electromagnet in the alignment compensator system to push the tracking probe in an amount proportional to the forward speed of the driven probe to correct for misalignment between the driven and tracking probes. An alignment sensor of an embodiment of the present invention may be adapted to be capable of providing information directly to a controller without using a decoder 266. An alignment sensor of an embodiment of the present invention may also be adapted to provide both direction and speed information about the driven probe to provide the alignment compensator system the ability to control power to one or more electromagnets based on the speed and/or direction of the driven probe. An alignment compensator, or an alignment compensator system, may be configured differently so long as the alignment compensator, or alignment compensator system, compensates for misalignments between driven and tracking probes. For example, instead of having an electromagnet of an alignment compensator destructively interfere with a portion of a ring magnet, an electromagnet of an alignment compensator could constructively interfere to pull, instead of push, a tracking probe.

Many modifications and other embodiments of the invention will come to mind to one skilled in the art having the benefit of the teachings presented in the foregoing descriptions and the associated drawings. Therefore, the invention should not be limited to the specific embodiments disclosed. Specific terms are used in a generic and descriptive sense only and not for purposes of limitation.

That which is claimed:

1. An alignment compensator for use with a magnetically coupled inspection probe, comprising
   a first electromagnet capable of at least partially altering the magnetic attraction of the magnetically coupled inspection probe;
   a variable power supply electrically connected to said first electromagnet; and
   a controller interoperably connected to said variable power supply, wherein said controller is capable of adjusting the power to said first electromagnet and, thereby, capable of adjusting the alteration of the magnetic attraction of the magnetically coupled inspection probe and correcting misalignments of the magnetically coupled inspection probe.

2. The alignment compensator of claim 1, further comprising an alignment sensor communicably connected to said controller.

3. The alignment compensator of claim 2, further comprising a decoder communicably connected to said controller and said alignment sensor and wherein said alignment sensor is a linear encoder.

4. The alignment compensator of claim 1, further comprising a second electromagnet interoperably connected to said variable power source, wherein said controller is capable of adjusting the power to said second electromagnet.

5. An apparatus for ultrasonically inspecting a structure, comprising:
 a driven probe structured for being disposed proximate a first surface of the structure, said driven probe comprising a magnet and a sensor for inspecting the structure as said driven probe is moved over the first surface of the structure; and
 a tracking probe structured for being disposed proximate an opposed second surface of the structure, said tracking probe also comprising a magnet for cooperating with said magnet of said driven probe to draw the driven and tracking probes toward the first and second surfaces of the structure, respectively, wherein magnetic attraction between said driven and tracking probes causes said tracking probe to be moved over the second surface of the structure in response to corresponding movement of said driven probe, and wherein at least one of said driven probe and said tracking probe comprise an alignment compensator capable of correcting misalignments between said sensor of said driven probe and said tracking probe.

6. The apparatus of claim 5, wherein said alignment compensator comprises a permanent magnet for at least partially altering the magnetic attraction between said driven probe and said tracking probe.

7. The apparatus of claim 6, wherein said alignment compensator further comprises an alignment magnet housing for supporting a magnet of said alignment compensator.

8. The apparatus of claim 5, wherein said alignment compensator comprises an electromagnet for at least partially altering the magnetic attraction between said driven probe and said tracking probe.

9. The apparatus of claim 8, wherein said alignment compensator further comprises:
 a variable power supply electrically connected to said electromagnet of said alignment compensator; and
 a controller interoperably connected to said variable power supply of said alignment compensator.

10. The apparatus of claim 9, wherein said controller is communicably connected to said sensor of said driven probe.

11. The apparatus of claim 10, wherein said controller is capable of adjusting power to said electromagnet based upon a signal received by said sensor of said driven probe and communicated to said controller.

12. The apparatus of claim 9, wherein said alignment compensator further comprises an alignment sensor communicably connected to said controller.

13. The apparatus of claim 12, wherein said controller is capable of adjusting power to said electromagnet based upon a signal received by said alignment sensor and communicated to said controller.

14. The apparatus of claim 9, wherein said tracking probe further comprises a sensor for receiving an ultrasonic signal from said sensor of said driven probe, and wherein said sensor of said tracking probe is communicably connected to said controller.

15. The apparatus of claim 14, wherein said controller is capable of adjusting power to said electromagnet based upon a signal received by said sensor of said tracking probe and communicated to said controller.

16. The apparatus of claim 5, wherein said alignment compensator comprises:
 at least two electromagnets spaced apart from one another;
 a variable power supply electrically connected to said electromagnets; and
 a controller interoperably connected to said variable power supply, wherein said controller is capable of independently controlling the power to the electromagnets.

17. The apparatus of claim 16, wherein said controller is capable of turning off at least one of said electromagnets.

18. The apparatus of claim 16, wherein said driven probe comprises an alignment compensator, wherein said magnet of said driven probe comprises a ring magnet, and wherein said alignment compensator comprises two electromagnets disposed on opposite sides of said ring magnet of said driven probe.

19. The apparatus of claim 18, wherein said controller adjusts power to said electromagnets depending upon the direction of movement of said driven probe with respect to said first surface.

20. The apparatus of claim 16, wherein said driven probe comprises an alignment compensator, wherein said magnet of said driven probe comprises a ring magnet, and wherein said alignment compensator comprises more than two electromagnets disposed around said ring magnet of said driven probe in a spaced apart relationship.

21. The apparatus of claim 20, wherein said controller adjusts power to said electromagnets depending upon the direction of movement of said driven probe with respect to said first surface.

22. A probe for inspecting a structure, comprising:
 a housing;
 a magnet disposed in said housing;
 a sensor disposed in said housing; and
 an alignment compensator carried by said housing and capable of correcting misalignments of magnetic coupling provided by the magnet.

23. The probe of claim 22, wherein said alignment compensator comprises a permanent magnet.

24. The probe of claim 23, wherein said alignment compensator further comprises an alignment magnet housing.

25. The probe of claim 22, wherein said alignment compensator comprises an electromagnet.

26. The probe of claim 25, wherein said alignment compensator further comprises:
 a variable power supply electrically connected to said electromagnet of said alignment compensator; and
 a controller interoperably connected to said variable power supply of said alignment compensator.

27. The probe of claim 26, wherein said controller is communicably connected to said sensor.

28. The probe of claim 27, wherein said controller is capable of adjusting power to said electromagnet based upon a signal received by said sensor and communicated to said controller.

29. The probe of claim 26, wherein said alignment compensator further comprises an alignment sensor communicably connected to said controller.

30. The probe of claim 29, wherein said controller is capable of adjusting power to said electromagnet based upon a signal received by said alignment sensor and communicated to said controller.

31. A method of inspecting a structure, comprising:
positioning a driven probe proximate a first surface of the structure and a tracking probe proximate an opposed second surface of the structure;
establishing magnetic attraction between the driven probe and the tracking probe such that the driven probe and the tracking probe are drawn toward the first and second surfaces of the structure, respectively;
moving the driven probe along the first surface of the structure which causes the tracking probe to be correspondingly moved along the second surface of the structure;
at least partially altering the magnetic attraction between the driven probe and the tracking probe by introducing an alignment compensating magnetic field to the magnetic attraction such that the resulting magnetic attraction is asymmetrical to align the driven probe and the tracking probe; and
transmitting ultrasonic signals into and receiving ultrasonic signals from the structure as the driven probe is moved along the first surface of the structure and the tracking probe is correspondingly moved along the second surface of the structure.

32. The method of aligning magnetically attracted probes of claim 31, wherein said step of altering the magnetic attraction comprises the step of actuating an electromagnet of the alignment compensator to compensate for misalignment between the driven probe and the tracking probe.

33. The method of aligning magnetically attracted probes of claim 32, wherein said step of altering the magnetic attraction further comprises the step of sensing the alignment between the driven probe and the tracking probe.

34. The method of aligning magnetically attracted probes of claim 33, wherein said step of sensing the alignment between the driven probe and the tracking probe comprises monitoring an ultrasonic signal received from at least one of the driven probe and the tracking probe.

35. The method of aligning magnetically attracted probes of claim 33, wherein said step of altering the magnetic attraction further comprises the steps of:
monitoring for a change in at least one of the characteristics selected from the group of velocity of movement of the driven probe and the tracking probe along the first and second surfaces respectively of the structure, acceleration of movement of the driven probe and the tracking probe along the first and second surfaces respectively of the structure, and vertical to horizontal position of the driven probe and the tracking probe along the first and second surfaces respectively of the structure; and
adjusting the magnetic field strength of at least one electromagnet of the alignment compensator to compensate for the monitored change.

36. The method of aligning magnetically attracted probes of claim 33, wherein said step of aligning the driven probe and the tracking probe further comprises the steps of:
monitoring for a reversal of direction of motion of the driven probe and the tracking probe along the first and second surfaces respectively of the structure; and
adjusting the magnetic field strength of at least two electromagnets of the alignment compensator to compensate for the reversal of direction, wherein said adjusting of power reverses alignment compensation between the at least two electromagnets.

37. The method of aligning magnetically attracted probes of claim 31, wherein said step of altering the magnetic attraction comprises the step of repositioning at least one magnet with respect to a position of transmission of ultrasonic signals from the driven probe and a position of reception of ultrasonic signals by the tracking probe.

38. The method of aligning magnetically attracted probes of claim 37, wherein said step of altering the magnetic attraction further comprises the step of sensing the alignment between the driven probe and the tracking probe.

39. The method of aligning magnetically attracted probes of claim 38, wherein said step of sensing the alignment between the driven probe and the tracking probe comprises monitoring an ultrasonic signal received from at least one of the driven probe and the tracking probe.

40. The method of aligning magnetically attracted probes of claim 38, wherein said step of repositioning at least one magnet comprises the step of monitoring for a change in at least one of the characteristics selected from the group of velocity of movement of the driven probe and the tracking probe along the first and second surfaces respectively of the structure, acceleration of movement of the driven probe and the tracking probe along the first and second surfaces respectively of the structure, and vertical to horizontal position of the driven probe and the tracking probe along the first and second surfaces respectively of the structure.

41. The method of aligning magnetically attracted probes of claim 38, wherein said step of repositioning at least one magnet comprises the step of monitoring for a reversal of direction of motion of the driven probe and the tracking probe along the first and second surfaces respectively of the structure.

* * * * *

UNITED STATES PATENT AND TRADEMARK OFFICE
CERTIFICATE OF CORRECTION

PATENT NO. : 7,228,741 B2
APPLICATION NO. : 10/943170
DATED : June 12, 2007
INVENTOR(S) : Gerogeson et al.

It is certified that error appears in the above-identified patent and that said Letters Patent is hereby corrected as shown below:

Column 21, claim 32, line 31, "aligning magnetically attracted probes" should read --inspecting a structure--;
claim 33, line 36, "aligning magnetically attracted probes" should read --inspecting a structure--;
claim 34, line 40, "aligning magnetically attracted probes" should read --inspecting a structure--;
claim 35, line 45, "aligning magnetically attracted probes" should read --inspecting a structure--;

Column 22, claim 36, line 8, "aligning magnetically attracted probes" should read --inspecting a structure--;
claim 37, line 19, "aligning magnetically attracted probes" should read --inspecting a structure--;
claim 38, line 26, "aligning magnetically attracted probes" should read --inspecting a structure--;
claim 39, line 30, "aligning magnetically attracted probes" should read --inspecting a structure--;
claim 40, line 35, "aligning magnetically attracted probes" should read --inspecting a structure--;
claim 41, line 46, "aligning magnetically attracted probes" should read --inspecting a structure--;

Signed and Sealed this

Seventeenth Day of March, 2009

JOHN DOLL
*Acting Director of the United States Patent and Trademark Office*